US006214791B1

(12) United States Patent
Arnon et al.

(10) Patent No.: US 6,214,791 B1
(45) Date of Patent: Apr. 10, 2001

(54) TREATMENT OF MULTIPLE SCLEROSIS THROUGH INGESTION OR INHALATION OF COPOLYMER-1

(75) Inventors: Ruth Arnon; Michael Sela; Dvora Teitelbaum, all of Rehovot; Adrian Gilbert, Kfar-Saba; Milka Linenberg, Tel-Mond; Rivka Riven-Kreitmann, Kfar-Saba, all of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/341,369

(22) PCT Filed: Jan. 12, 1998

(86) PCT No.: PCT/US98/00375

§ 371 Date: Jan. 12, 2000

§ 102(e) Date: Jan. 12, 2000

(87) PCT Pub. No.: WO98/30227

PCT Pub. Date: Jul. 16, 1998

(30) Foreign Application Priority Data

Jan. 10, 1997 (IL) .......................................... 119989

(51) Int. Cl.⁷ .................................................. A61K 38/00

(52) U.S. Cl. ................................................................ 514/2

(58) Field of Search .................................................. 514/2

(56) References Cited

U.S. PATENT DOCUMENTS

| | | | |
|---|---|---|---|
| 3,849,550 | * 11/1974 | Teitelbaum et al. | 424/78 |
| 4,339,431 | 7/1982 | Gaffar . | |
| 5,204,099 | 4/1993 | Barbier et al. . | |
| 5,627,206 | * 5/1997 | Hupe et al. | 514/468 |
| 5,719,296 | 2/1998 | Action, III et al. . | |
| 5,981,581 | * 11/1999 | Konkino et al. | 515/561 |

FOREIGN PATENT DOCUMENTS

| | | |
|---|---|---|
| 383620A2 | 8/1990 | (EP) . |
| WO9533475 | 12/1995 | (WO) . |

OTHER PUBLICATIONS

Chem. abstr., vol. 125, No. 23, Dec. 2, 1996 (Columbus OH, USA), p. 1, column 2, the abstract No. 291993b, Johnson, K.P., et al., 'Management of Relapsing/Remitting Multiple Sclerosis with Copolymer 1 (Copaxone).' Mult. Scler. 1996, 1(6), 325–326 (Eng.), see entire document.
Teitelbaum et al., "Suppression of Experimental Allergic Encephalomyelitis by a Synthetic Polypeptide", *Israel J. Med. Sci.*, 1971, 7, 630–631 (Abstract) (Exhibit 6).
Teitelbaum et al., "Suppression of Experimental Allergic Encephalomyelitis by a Synthetic Polypeptide", *Eur. J. Immunol.*, 1971, 1, 242–248 (Exhibit 7).
Arnon et al., "Suppression of Experimental Allergic Encephalomyelitis by a Synthetic Copolymer Immunological Cross Reactive with Basic Encephalitogen", *Israel J. Med. Sci.*, 1972, 8, 1759–1760 (Exhibit 8).
Teitelbaum et al., "Protection Against Experimental Allergic Encephalomyelitis", *Nature,* 1972, 240, 564–566 (Exhibit 9).
Webb et al., "Further Studies on the Suppression of Experimental Allergic Encephalomyelitis by Synthetic Copolymer", *Israel J. Med. Sci.,* 1972, 8, 656–657 (Exhibit 10).
Teitelbaum et al., "Suppression of Experimental Allergic Encephalomyelitis with Basic Polymers", *Eur. J. Immunol.,* 1973, 3, 273–279 (Exhibit 11).
Webb et al., "In Vivo and in Vitro Immunological Cross–reactions between Basic Encephalitogen and Synthetic Basic Polypeptides Capable of Suppressing Experimental Allergic Encephalomyelitis", *Eur. J. Immunol,* 1973, 3, 279–286 (Exhibit 12).
Teitelbaum et al., "Dose–response Studies on Experimental Allergic Encephalomyelitis Suppression by Cop–1", *Israel. J. Med. Sci.,* 1974, 10(9), 1172–1173 (Exhibit 13).
Teitelbaum et al., "Suppression of Experimental Allergic Encephalomyelitis in Rhesus Monkeys by a Synthetic Basic Copolymer", *Clin. Immunol. Immunopath.,* 1974, 3, 256–262 (Exhibit 14).
Webb et al., "Suppression of Experimental Allergic Encephalomyelitis in Rhesus Monkeys by a Synthetic Basic Copolymer", *Isr. J. Med. Sci.,* 1975, 11, 1388 (Abstract) (Exhibit 15).
Webb et al., "Molecular Requirements Involved in Suppression of EAE by Synthetic Basic Copolymers of Amino Acids", *Immunochem.,* 1976, 13, 333–337 (Exhibit 16).
Abramsky et al., "Effect of a Synthetic Polypeptide (Cop–1) on Patients with Multiple Sclerosis and with Acute Disseminated Encephalomyelitis", *J. Neurol. Sci.,* 1977, 31, 433–438 (Exhibit 17).
Teitelbaum et al., "Suppression of Experimental Allergic Encephalomyelitis in Baboons by Cop 1", *Israel J. Med. Sci.,* 1977, 13, 1038 (Abstract) (Exhibit 18).
Arnon et al., "Suppression of EAE in Baboons by a Synthetic Polymer of Amino Acids", *Neurol.,* 1978, 28, 336 (Abstract) (Exhibit 19).
Sela et al., "Experimental Allergic Encephalomyelitis" in *Menarini Series on Immunopathology,* vol. 1, First Symposium of Organ Specific Autoimmunity, Cremona, Italy, Jun., 1977, (Miescher P.A. ed., Schwabe Co., Basel, 1978), 9–21 (Exhibit 20).

(List continued on next page.)

*Primary Examiner*—James H. Reamer
(74) *Attorney, Agent, or Firm*—John P. White; Cooper & Dunham LLP

(57) ABSTRACT

The present invention relates to the treatment of multiple sclerosis by ingestion or inhalation of copolymet-1 and pharmaceutical compositions useful for such treatment.

15 Claims, 8 Drawing Sheets

OTHER PUBLICATIONS

Alvord et al., "Myelin Basic Protein Treatment of Experimental Allergic Encephalomyelitis in Monkeys", *Ann. Neurol.*, 1979, 6, 469–473 (Exhibit 21).

Keith et al., "The Effect of Cop 1, a Synthetic Polypeptide, on Chronic Relapsing Experimental Allergic Encephalomyelitis in Guinea Pigs" *J. Neurol. Sci.*, 1979, 42, 267–274 (Exhibit 22).

Lando et al., "Effect of Cyclophosphamide on Suppressor Cell Activity in Mice Unresponsive to EAE", *J. Immunol.*, 1979, 123, 2156–2160. (Abstract) (Exhibit 23).

Lando et al., "Experimental Allergic Encephalomyelitis in Mice—Suppression and Prevention with Cop–1", *Israel J. Med. Sci.*, 1979, 15, 868–869 (Abstract) (Exhibit 24).

Teitelbaum et al., "Blocking of Sensitization to Encephalitogenic Basic Protein in Vitro by Synthetic Basic Copolymer (Cop 1)"in *Cell Biology and Immunology of Leukocyte Function* (Academic Press, New York, 1979) 681–685 (Exhibit 25).

Teitelbaum, "Suppression of Experimental Allergic Encephalomyelitis with a Synthetic Copolymer—Relevance to Multiple Sclerosis", in *Humoral Immunity in Neurological Diseases* (Karcher D., Lowenthal A. & Strosberg A.D., eds., Plenum Publishing Corp., 1979) 609–613 (Exhibit 26).

Arnon et al., "Desensitization of Experimental Allergic Encephalomyelitis with Synthetic Peptide Analogues" in *The Suppression of Experimental Allergic Encephalomyelitis and Multiple Sclerosis* (Academic Press, New York, 1980) 105–107 (Exhibit 27).

Arnon, "A Synthetic Copolymer of Amino Acids in a Clinical Trial for MS Therapy" in *Progress in Multiple Sclerosis Research* (Bauer, Ritter, eds., Springer Verlag, New York, 1980) 416–418 (Exhibit 28).

Bornstein et al., "Treatment of Multiple Sclerosis with a Synthetic Polypeptide: Preliminary Results", *Ann. Neurol.*, 1980, 8, 117 (Abstract) (Exhibit 29).

Bornstein et al., "Treatment of Multiple Sclerosis with a Synthetic Polypeptide: Preliminary Results", *Trans. Am. Neurol. Assoc.*, 1980, 105, 348–350 (Exhibit 30).

McDermott et al., "Antigen–induced Suppression of Experimental Allergic Neuritis in the Guinea Pig", *J. Neurol. Sci.*, 1980, 46 137–143 (Exhibit 31).

Arnon, "Experimental Allergic Encephalomyelitis—Susceptibility and Suppression", *Immunological Rev.*, 1981, 55, 5–30 (Exhibit 32).

Bornstein et al., "Multiple Sclerosis: Trial of a Synthetic Polypeptide", *Ann. Neurol.*, 1982, 11, 317–319 (Exhibit 33).

Brosnan et al., "The Response of Normal Human Lymphocytes to Copolymer 1", *J. Neuropath. Exp. Neurol.*, 1983, 42, 356 (Abstract) (Exhibit 34).

Lisak et al., "Effect of Treatment with Copolymer 1 (Cop–1) on the in Vivo and in Vitro Manifestations of Experimental Allergic Encephalomyelitis (EAE)", *J. Neurol. Sci.*, 1983, 62, 281–293 (Exhibit 35).

Bornstein et al., "Clinical Trials of Copolymer 1 in Multiple Sclerosis", *Ann. N.Y. Acad. Sci. (USA)*, 1984, 366–372 (Exhibit 36).

Bornstein et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144–150 (Exhibit 37).

Brosnan et al., "Copolymer 1: Effect on Normal Human Lymphocytes", *Ann. N.Y. Acad. Sci (USA)*, 1984, 436, 498–499 (Exhibit 38).

Bornstein et al., "Multiple Sclerosis: Clinical Trials of a Synthetic Polypeptide, Copolymer 1", *Neurol.*, 1985, 35 (Suppl. 1), 103 (Abstract) (Exhibit 39).

Brosnan et al., "Immunogenic Potentials of Copolymer 1 in Normal Human Lymphocytes", *Neurol.*, 1985, 35, 1754–1759 (Exhibit 40).

Burns et al., "Human Cellular Immune Response in Vitro to Copolymer 1 and Myelin Basic Protein (MBP)", *Neurol.*, 1985, 35 (Suppl. 1), 170 (Abstract) (Exhibit 41).

Teitelbaum et al., "Monoclonal Antibodies to Myelin Basic Protein Cross React with Synthetic EAE–suppressive Copolymer, Cop 1" in *Proc. 7th Eur. Immunol. Mtg.*, Jerusalem, Sep. 8–13, 1985 (Abstract) (Exhibit 42).

Thompson, "MCQ Tutor: Medical Immunology Multiple Choice Questions", *Immunol. Today*, 1985, 6(4), 141 (Exhibit 43).

Burns et al., "Human Cellular Immune Response to Copolymer 1 and Myelin Basic Protein", *Neurol.*, 1986, 36, 92–94 (Exhibit 44).

Bornstein, "Cop 1 may be Beneficial for Patients with Exacerbating–remitting Form of Multiple Sclerosis", *Adv. Ther. (USA)*, 1987, 4, 206 (Abstract) (Exhibit 45).

Bornstein et al., "A Pilot Trial of Cop 1 in Exacerbating–remitting Multiple Sclerosis", *New Eng. J. Med.*, 1987, 317(7), 408–414 (Exhibit 46).

Rolak, "Copolymer–I Therapy for Multiple Sclerosis", *Clin. Neuropharmacology*, 1987, 10(5), 389–396 (Exhibit 47).

Winer, "Cop 1 Therapy for Multiple Sclerosis", *New Eng. J. Med.*, 1987, 317(7), 442–444 (Exhibit 48).

Arnon et al., "Suppression of Demyelinating Diseases by Synthetic Copolymers", in *A Multidisciplinary Approach to Myelin Disease* (G. Serlupi Crescenzi, ed., Plenum Publishing Corp., 1988) 243–250 (Exhibit 49).

Baumhefner et al., "Copolymer 1 as Therapy for Multiple Sclerosis: The Cons", *Neurol.*, 1988, 38(Suppl. 2), 69–71 (Exhibit 50).

Bornstein et al., "Clinical Experience with Cop–1 in Multiple Sclerosis", *Neurol.*, 1988, 38(Suppl. 2), 66–69 (Exhibit 51).

Teitelbaum et al., "Specific Inhibition of the T–cell Response to Myelin Basic Protein by the Synthetic Copolymer Cop 1" *Proc. Natl. Acad. Sci. USA*, 1988, 85 9724–9728 (Exhibit 52).

Arnon et al., "Suppression of Experimental Allergic Encephalomyelitis by Cop–1—Relevance to Multiple Sclerosis", *Israel J. Med. Sci.*, 1989, 25, 686–689 (Exhibit 53).

Bornstein et al., "Pilot Trial of Cop–1 in Chronic Progressive Multiple Sclerosis: Preliminary Report", from *The International Multiple Sclerosis Conference: An update on Multiple Sclerosis*, Roma (Italy), Sep. 15–17, 1988, in Elsevier Science Publisher, 1989, 225–232 (Exhibit 54).

Teitelbaum et al., "Clinical Trial of Copolymer 1 in Multiple Sclerosis", *J. Israel Med. Assoc.*, 1989, CXVI(9), 453–456 (Exhibit 55).

Bornstein et al., "Clinical Trials of Cop 1 in Multiple Sclerosis" in *Handbook of Multiple Sclerosis* (S.D. Cook Marcel Rekker, ed., 1990) 469–480 (Exhibit 56).

Carter et al., "Newer Drug Therapies for Multiple Sclerosis", *Drug Therapy*, 1990, 31–32, 37–39, 42–43 (Exhibit 57).

Grgacic et al., "Cell–mediated Immune Response to Copolymer 1 in Multiple Sclerosis Measured by the Macrophage Procoagulant Activity Assay", *Int. Immunol.*, 1990, 2(8), 713–718 (Exhibit 58).

Kay et al., "The Mechanism of Action of FK 506", *Transplantation Proceedings*, 1990, 22(1, Suppl. 1), 96–99 (Exhibit 59).

Myers et al., "The Peculiar Difficulties of Therapeutic Trials for Multiple Sclerosis", *Neurologic Clinics*, 1990 8(1), 119–141 (Exhibit 60).

Sela et al., "Suppressive Activity of Cop–1 in EAE and its Relevance to Multiple Sclerosis", *Bull. Inst. Pasteur*, 1990, 88, 303–314 (Exhibit 61).

Stazl, *Transplantation Proceedings*, 1990, 22 (1, Suppl. 1), 5 (Exhibit 62).

Wender, "Copolymer 1 (Cop–1) in the Treatment of Multiple Sclerosis (letter)" *Neuro. Neurochir. Pol.*, 1990, 24, 113 (Exhibit 63).

Bornstein et al., "A Placebo–controlled, Double–blind, Randomized Two–center, Pilot Trial of Cop 1 in Chronic Progressive Multiple Sclerosis", *Neurol.*, 1991, 41, 533–539 (Exhibit 64).

Burns et al., "Failure of Copolymer 1 to Inhibit the Human T–cell Response to Myelin Basic Protein", *Neurol.*, 1991, 41, 1317–1319, (Exhibit 65).

Clinical Trial Protocol No. 9001, Teva Pharmaceutical Industries, Ltd., first patient enrolled Oct. 23, 1991 (Exhibit 66).

Ferrara et al., "Graft–Versus–Host Disease", *New Eng. J. Med.*, 1991, 324, 667–674 (Exhibit 67).

Meiner, "Cop–1 Multicenter Clinical Trial in Exacerbating–remitting Multiple–Sclerosis: One Year Follow–up", *J. Neurol.*, 1991(Suppl. 1) (Abstract) (Exhibit 68).

Rothbard et al., "Interactions Between Immunogenic Peptides and MHC Proteins", *Ann. Rev. Immunol.*, 1991, 9, 527–565 (Exhibit 79).

Salvetti et al., "Myelin Basic Protein T Cell Epitopes in Patients with Multiple Sclerosis", *Department of Neurological Sciences*, University of Rome, La Sapienza, 1991, 72 (Abstract) (Exhibit 70).

Teitelbaum et al., "Cross–reactions and Specificities of Monoclonal Antibodies Against Myelin Basic Protein and Against the Synthetic Copolymer 1", *Proc. Natl. Acad. Sci. (USA)*, 1991, 88, 9528–9532 (Exhibit 71).

Van den Bogaerde et al., "Induction of Long–Term Survival of Hamster Heart Xenografts in Rats", *Transplantation*, 1991, 52, 15–20 (Exhibit 72).

Bornstein et al., "Treatment of Multiple Sclerosis with Copolymer 1" in *Treatment of Multiple Scleorsis: Trial Design, Results and Future Perspectives*(Rudick R.A. & Goodkin D.E., eds., Springer Verlag, London, 1992) 173–198 (Exhibit 73).

Johnson, "Clinical Studies in Copolymer 1 Therapy for Exacerbating–remitting Multiple Sclerosis", in *Congress for Advances in the Understanding and Treatment of Multiple Sclerosis*, Boston (USA), Oct. 28–29, 1992 (Exhibit 74).

Milo et al., "Inhibition of Myelin Basic Protein–specific Human T–cell Lines by Cop–1", *Israel J. Med. Sci.*, 1992, 28, 486 (Abstract) (Exhibit 75).

Racke et al., "Copolymer–1–induced Inhibition of Antigen–specific T Cell Activation: Interference with Antigen Presentation", *J. Neuroimmunol.*, 1992, 37, 75–84 (Exhibit 76).

Teitelbaum et al., "Synthetic Copolymer 1 Inhibits Human T–cell Lines Specific for Myelin Basic Protein", *Proc. Natl. Acad., Sci. (USA)*, 1992, 89, 137–141 (Exhibit 77).

Weinshenker et al., "Natural History and Treatment of Multiple Sclerosis", *Current Opinion in Neurol. and Neurosurgery*, 1992, 5, 203–211 (Exhibit 78).

Aharoni et al., "T Suppressor Hybridomas and Interleukin–2–Dependent Lines Induced by Copolymer 1 or by Spinal Cord Homogenate Down–Regulate Experimental Allergic Encephalomyelitis", *Eur. J. Immunol.*, 1993, 23, 17–25 (Exhibit 79).

Arnon et al., "Immunomodulation of Experimental Allergic Encephalomyelitis", *Israel J. Med. Sci.*, 1993, 29, 175–181 (Exhibit 80).

Arnon et al., "On the Existence of Suppressor Cells", *Int. Arch. Allergy Immunol.*, 1993, 100, 2–7 (Exhibit 81).

Clinical Trial Protocol No. 9002, Lemmon Co. and Teva Pharmaceutical Industries, Ltd., first patient enrolled Jun. 17, 1993 (Exhibit 82).

Francis, "The Current Therapy of Multiple Sclerosis", *J. Clin. Pharmacy and Therapeutics*, 1993, 18, 77–84 (Exhibit 83).

Keleman et al., "Graft–versus–Host Disease in Bone Marrow Tranplantation: Experimental, Laboratory, and Clinical Contributions of the Last Few Years", *Int. Arch. Allergy Immunol.*, 1993, 102, 309–320 (Exhibit 84).

Gurevich, "Study of the MHC–competition Between BP and Cop 1 Using Human Cytotoxic T–cell Clones", *Isr. J. Med. Sci.*, 1993 (Abstract) (Exhibit 85).

Meiner et al., "The Israeli Cop–1 Multicenter Clinical Trial in Exacerbating–remitting Multiple Sclerosis—Two–year Follow–up", in *9$^{th}$ Congress of the European Committee for Treatment and Research in Multiple Sclerosis*, Florence (Italy), Oct.–Nov., 1993, 48 (Abstract) (Exhibit 86).

Milo et al., "Copolymer–1 (Cop–1) Regulated Class II MHC Expression and Cytokine Synthesis in the THP–1 Monocyte–Macrophage Cell Line" in *The IBC Conference on Multiple Sclerosis*, San Diego (USA), Dec. 10, 1993 (Abstract) (Exhibit 87).

Sela, "Polymeric Drugs as Immunomodulatory Vaccines Against Multiple Sclerosis", *Makromol. Chem. Macromol. Symp.*, 1993, 70/71, 147–155 (Exhibit 88).

Arnon et al., "Immunospecific Drug Design—Prospects for Treatment of Autoimmune Disease", *Therapeutic Immunol.*, 1994, 1, 65–70 (Exhibit 89).

Bansil et al., "Multiple Sclerosis: Pathogenesis and Treatment", *Seminars in Neurol.*, Jun. 1994, 14(2), 146–153 (Exhibit 90).

The Cop–1 Multicenter Clinical and Research Group Study, "Cop–1 Multicenter Trial in Relapsing Remitting Multiple Sclerosis: 3 Year Follow Up", *Abstracts of Symposia and Free Communication*, Barcelona (Spain), Jun. 25–29, 1994, 241 (Suppl. 1), 6 (Exhibit 91).

Cotton, "Options for Multiple Sclerosis Therapy", *J.A.M.A. Medical News & Perspectives*, 1994, 272(18), 1393 (Exhibit 92).

Dorling et al., "Prospects for Xenografting", *Curr. Opinions Immunol.*, 1994, 6, 765–769 (Exhibit 93).

Fridkis–Hareli et al., "Copolymer 1 Displaces MBP, PLP and MOG, but Can Not be Displaced by these Antigens from the MHC Class II Binding Site", *Department of Chemical Immunology, The Weizmann Institute of Science*, 1994 (Exhibit 94).

Fridkis–Hareli et al., "Direct Binding of Myelin Basic Protein and Synthetic Copolymer 1 to Class II Major Histocompatibility Complex Molecules on Living Antigen–Presenting Cells—Specificity and Promiscuity", *Proc. Natl. Acad. Sci. USA,* 1994, 91, 4872–4876 (Exhibit 95).

Fridkis–Hareli et al., "Specific and Promiscuous Binding of Synthetic Copolymer 1 to Class II Major Histocompatibility Complex Molecules on Living Antigen Presenting Cells", *Israeli Biochem. Soc.,* 1994, 21–22 (Abstract) (Exhibit 96).

Fridkis–Hareli et al., "Synthetic Copolymer 1 Inhibits the Binding of MBP, PLP and MOG Peptides to Class II Major Histocompatibility Complex Molecules on Antigen Presenting Cells" in *Neurochem Mtg.,* Aug. 14–19, 1994 (Exhibit 97).

Fridkis–Hareli et al., Synthetic Copolymer 1 Inhibits the Binding of MBP, PLP and MOG Peptides to Class II Major Hisotcompatibility Complex Molecules on Antigen–Presenting Cells, *J. Neurochem.,* 1994, 63(Suppl. I), 561 (Exhibit 98).

Fridkis–Hareli et al., "Synthetic Copolymer 1 and Myelin Basic Protein do not Require Processing Prior to Binding to Class II Major Histocompatibility Complex Molecules on Living Antigen Presenting Cells", *Department of Chemical Immunology, The Weizmann Institute of Science,* Rehovot, Israel, 1994 (Exhibit 99).

Fridkis–Hareli et al., "Synthetic Copolymer 1 and Myelin Basic Protein Do Not Undergo Processing Prior to the Binding to Class II Major Histocompatibility Complex Molecules on Antigen Presenting Cells", *Israeli Immunol. Soc.,* May 3–4, 1994 (Abstract) (Exhibit 100).

Jacobs et al., "Advances in Specific Therapy for Multiple Sclerosis", *Neurol.,* 1994, 7, 250–254 (Exhibit 101).

Johnson, "Experimental Therapy of Relapsing–Remitting Multiple Sclerosis with Copolymer–1", *Ann. Neurol.,* 1994, 36(Suppl.), 115–117 (Exhibit 102).

Kott et al., "Cop–1 Increases Suppressor Cells Number in Multiple Sclerosis", *Israel Neurological Assoc.,* Dec. 19–20, 1994, Herzliya (Israel), 17 (Exhibit 103).

Mengle–Gaw, "The Major Histocompatibility Complex (MHC)", in *Encycl. Molecular Bio.* (Oxford Blackwell Science Ltd, 1994) 602–606 (Exhibit 104).

Milo et al., "Additive Effects of Cop–1 and IFN–Beta on Immune Responses to Myelin Basic Protein", *Neurol.,* 1994, 44(Suppl. 2), A212 (Exhibit 105).

Milo et al., "Additive Effect of Copolymer–1 and Interferonβ on the Immune Response to Myelin Basic Protein", Assaf Harofeh Medical Center, Sackler School of Medicine, Tel–Aviv University of Maryland School of Medicine, 1994, 22 (Exhibit 106).

Milo et al., "Copolymer–1 and Interferon–β Additively Suppress the Immune Response to Myelin Basic Protein by Inhibiting Antigen Presentation", *J. Neuroimmunol.,* 1994, 54, 183 (Abstract) (Exhibit 107).

Nightingale et al., "Access to Investigational Drugs for Treatment Purposes", *Am. Family Physician,* 1994, 50(4) 845–847 (Exhibit 108).

Schlegel et al., "Prevention of Graft–Versus–Host Disease by Peptides Binding to Class II Major Histocompatibility Complex Molecules", *Blood,* 1994, 84(8), 2802–2810 (Exhibit 109).

Stark, "Expanded Clinical Trials of Treatments for Multiple Sclerosis (MS): Copolymer 1 (Cop–1) Treatment Investigational New Drug (IND) Program", *Ann. Neurol.,* 1994, 36, 114–115 (Exhibit 110).

Teitelbaum et al., "Immunological Parameters in a Multicenter Clinical Trial of Cop1 in Multiple Sclerosis (MS): A 2–year Follow–up", *Neurol.,* 1994, 44(Suppl. 2), A358 (Exhibit 111).

Fridkis–Hareli et al., "Synthetic Copolymer 1 and Myelin Basic Protein Do Not Require Processing Prior to Binding to Class II Major Histocompatibility Complex Molecules on Living Antigen–Presenting Cells", *Cell. Immunol.,* 1995, 163, 229–236 (Exhibit 112).

Milo et al., "Additive Effects of Copolymer–1 and Interferon β–1b on the Immune Response to Myelin Basic Protein", *J. Neuroimmunol.,* 1995, 61, 185–193 (Exhibit 113).

Schlegel et al., "Inhibition of Allorecognition and Prevention of Graft–vs–host Disease (GVHD) by GLAT, a Synthetic Polymer with Promiscuous Binding to Murine and Human MHC Class II Molecules", in *Am. Soc. Hematology,* 37$^{th}$ Annual Meeting, Seattle, WA (USA), Dec. 1–5, 1995, 224a (Abstract) (Exhibit 114).

Ben–Nun et al., "The Autoimmune Reactivity to Myelin Oligodendrocyte Glycoprotein (MOG)in Multiple Sclerosis is Potentially Pathogenic: Effect of Copolymer 1 on MOG–induced Disease", *J. Neurol.,* 1996, 243(Suppl. 1), S14–S22 (Exhibit 115).

Johnson, Management of Relapsing/Remitting Multiple Sclerosis with Copolymer 1 (Copaxone), Chemical Abstracts, 1996, 125, 291993b (Exhibit 116).

Sykes, "Immunobiology of Transplantation" *Faseb J.,* 1996, 10, 721–730 (Exhibit 117).

Teitelbaum et al., "Copolymer 1 Inhibits Chronic Relapsing Experimental Allergic Encephalomyelitis Induced by Proteolipid Protein (PLP) Peptides in Mice and Interferes with PLP–specific T Cell Responses", *J. Neuroimmunol.,* 1996, 64, 209–217 (Exhibit 118); and.

Durelli, "Immunotherapeutics of Multiple Sclerosis", *Istituto di Clinical delle Malattie del Sistema Nervoso Universita di Torino,* 467–475 (Exhibit 119).

\* cited by examiner

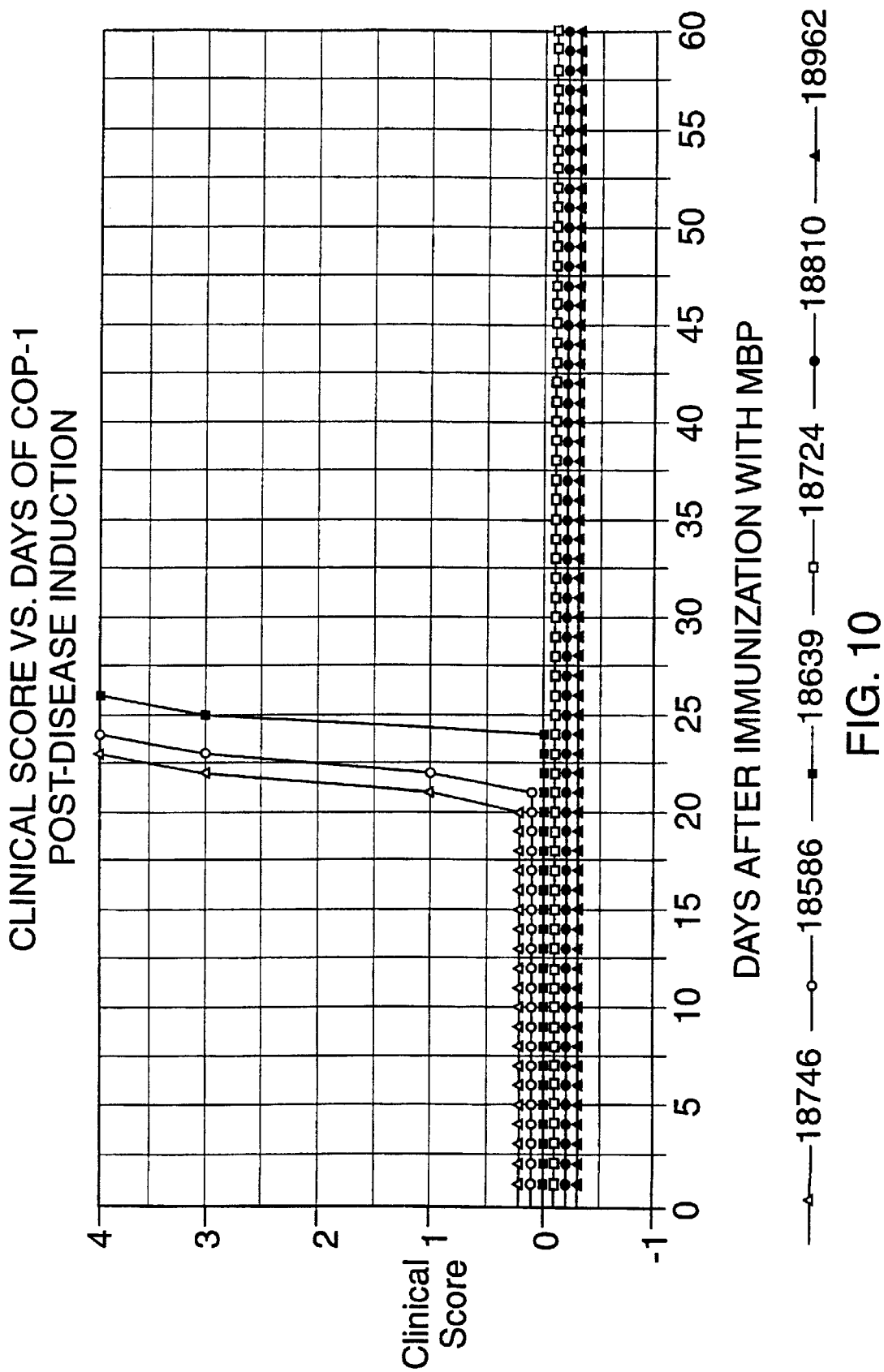

TREATMENT OF MULTIPLE SCLEROSIS THROUGH INGESTION OR INHALATION OF COPOLYMER-1

This application is a 371 of PCT/US98/00375, filed Sep. 12, 1998.

FIELD OF THE INVENTION

This invention relates to the treatment of multiple sclerosis by ingestion or inhalation of copolymer-1 (as defined below). The present invention also relates to a pharmaceutical composition comprising copolymer-1 used for the treatment of multiple sclerosis, wherein the pharmaceutical composition is formulated for administration by ingestion or inhalation.

BACKGROUND OF THE INVENTION

Copolymer-1, also known as glatiramer acetate and marketed under the tradename Copaxone®, comprises the acetate salts of polypeptides containing L-glutamic acid, L-alanine, L-tyrosine and L-lysine. The average molar fraction of the amino acids are 0.141, 0.427, 0.095 and 0.338, respectively, and the average molecular weight of copolymer-1 is between 4,700 and 11,000 daltons. It is a non-autoantigen which has been demonstrated to suppress experimental allergic encephalomyelitis (EAE) induced by various encephalitogens including mouse spinal cord homogenate (MSCH) which includes all myelin antigens, such as myelin basic protein (MBP) (Sela M et al., *Bull Inst Pasteur* (1990) 88 303–314), proteolipid protein (PLP) (Teitelbaum D et al., *J Neuroimmunol* (1996) 64 209–217) and myelin oligodendrocyte glycoprotein (MOG) (Ben-Nun A et al., *J Neurol* (1996) 243 (Suppl 1) S14–S22) in a variety of species. EAE is an accepted model for multiple sclerosis.

Copolymer-1 has been demonstrated to be active when injected subcutaneously, intra-peritoneally, intravenously or intramuscularly (D. Teitelbaum et al., *Eur. J. Immunol.* (1971) 1:242–248; D. Teitelbaum et al., *Eur. J. Immunol.* (1973) 3:273–279).

In phase III clinical trials, daily subcutaneous injections of copolymer-1 were found to slow progression of disability and reduce the relapse rate in exacerbating-remitting multiple sclerosis (K. P. Johnson, *Neurology* (1995) 1:65–70). Copolymer-1 therapy is presently limited to its daily subcutaneous administration.

Currently, all specifically approved treatments of multiple sclerosis involve self-injection of the active substance. Frequently observed injection-site problems include irritation, hypersensitivity, inflammation, pain and even necrosis (in the case of at least one interferon β 1-B treatment) and a low level of patient compliance. Therefore, an alternative method of administration is desirable.

EP Patent 359,783 discloses the treatment of autoimmune diseases by oral administration of autoantigens. It discloses the oral administration of MBP for treatment of multiple sclerosis. Oral administration of an autoantigen has been termed "oral tolerance."

PCT International Application Publication Nos. WO 91/12816, WO 91108760, and WO 92/06704 all disclose the treatment of other autoimmune diseases using the "oral tolerance" method with a variety of autoantigens. However, none of these references disclose the treatment of multiple sclerosis by the oral administration of non-autoantigen copolymer-1. The contents of all these patents and all literature references referred to above are hereby incorporated by reference in their entirety.

It is, therefore, an object of the present invention to provide a method for treating multiple sclerosis by oral administration of copolymer-1 through ingestion or inhalation.

BRIEF DESCRIPTION OF THE FIGURES

FIG. 10 shows the Clinical Scores vs. Days of Copolymer-1 Post EAE Disease Induction in six Rhesus Monkeys, in a trial comparing enteric-coated vs. uncoated pharmaceutical dosage form. Values at zero (0) have been separated on the y-axis to better show the results.

DETAILED DESCRIPTION OF THE INVENTION

Figure 1:
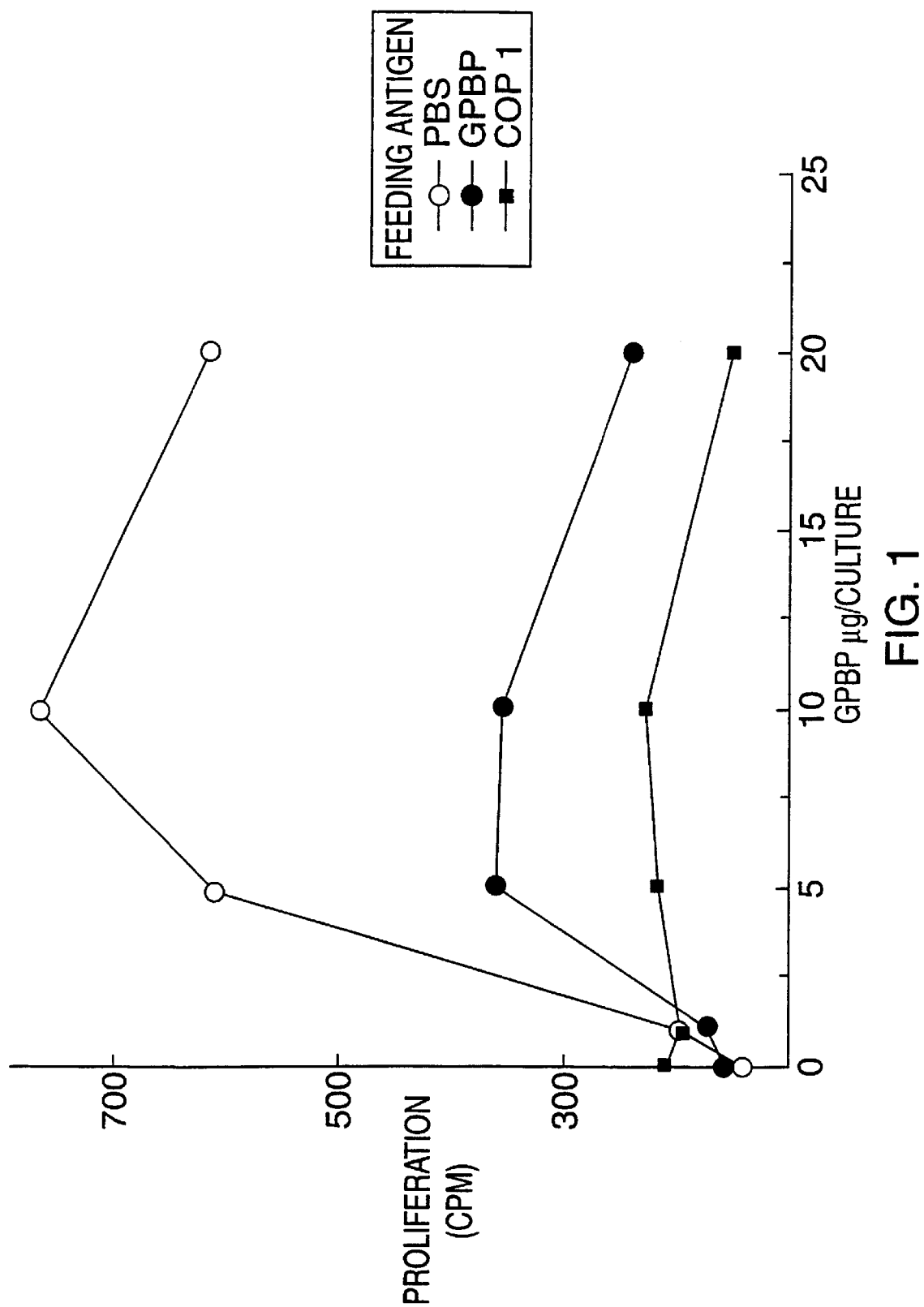
FIGS. 1 and 2 show the effect of copolymer-1 on the immune response to guinea pig myelin basic protein (GPBP) in rats (FIG. 1) and mice (FIG. 2) as assessed by spleen cell proliferation.

Accordingly, the present invention relates to the use of copolymer-1 in the preparation of a medicament for the treatment of multiple sclerosis. The medicament is administrated through either ingestion or inhalation.

The present invention is also directed to a method of treating multiple sclerosis comprising administration of a therapeutically effective amount of copolymer-1, wherein the administration is through either ingestion or inhalation.

The present invention is further directed to a pharmaceutical composition administered through ingestion or inhalation comprising a pharmaceutically acceptable carrier and a therapeutically effective amount of copolymer-1, wherein the pharmaceutical composition is used to treat multiple sclerosis.

As stated above, copolymer-1 comprises the acetate salts of polypeptides containing L-glutamic acid, L-alanine, L-tyrosine and L-lysine. The average molar fraction of the amino acids are 0.141, 0.427, 0.095 and 0.338, respectively, and the average molecular weight of copolymer-1 is between 4,700 and 11,000 daltons.

The present invention is based on the observation that, for example, the oral administration of copolymer-1 is effective in suppressing EAE, and, therefore, has a therapeutic value for the treatment of multiple sclerosis.

As contemplated, the copolymer-1 is brought into contact with those lymphoid tissues in the mucosal linings which are believed to be a primary source of immune system sensitization. These mucosal linings may be found (though not necessarily exclusively) in the sinuses, trachea, bronchial passages (where they are known as the BALT or bronchi-associated lymphoid tissues) and gastrointestinal linings (known as GALT or gut-associated lymphoid tissues). Thus, the administration of copolymer-1 is understood to include methods wherein copolymer-1 is introduced into the body by way of ingestion or inhalation. For example, copolymer-1 may be administered by way of the mouth through feeding, through a stomach tube, by inhalation into the bronchial passages or by nasal inhalation.

In one exemplary embodiment of the present invention, copolymer-1 is introduced orally in an amount of from 0.1 to 1000 mg per day, which may be administered as a single dose or in multiple dosages. As understood by one skilled in the art, the therapeutically effective dosage is generally a function of a patient's age, sex, and physical condition, as well as a function of other concurrent treatments being administered. The determination of the optimum, therapeutically effective dosage is well within the scope of one skilled in the art.

When copolymer-1 is introduced orally, it may be mixed with other food forms and consumed in solid, semi-solid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings are well known in the art. For example, K. Lehman, Acrylic Coatings in Controlled Release Tablet Manufacturer, *Manufacturing Chemist and Aerosol News*, p. 39 (June 1973), and K. Lehman, Programmed Drug Release From Oral Program Forms; *Pharma. Int.*, vol. ISS 3 1971, p. 34–41, teach enteric coatings such as Eudragit S and Eudragit L. *Handbook of Pharmaceutical Excipients,* 2nd ed., also teaches Eudragit S and Eudragit L applications. One Eudragit which may be used in the present invention is L30D55.

Copolymer-1 may also be administered nasally in certain of the above-mentioned forms by inhalation or nose drops. Furthermore, oral inhalation may be employed to deliver copolymer-1 to the mucosal linings of the trachea and bronchial passages.

Copolymer-1 may be prepared by methods known in the art, for example, as disclosed in U.S. Pat. No. 3,849,550, wherein the N-carboxyanhydrides of tyrosine, alanine, γ-benzyl glutamate and ε-N-trifluoroacetyllysine are polymerized at ambient temperature in anhydrous dioxane with diethylamine as an initiator. The deblocking of the γ-carboxyl group of the glutamic acid is effected by hydrogen bromide in glacial acetic acid and is followed by the removal of the trifluoroacetyl groups from the lysine residues by 1M piperidine.

As described in PCT/WO95/31990, copolymer-1 having a desired average molecular weight of about 7±2 kilodaltons may preferably be prepared by a method comprising reacting protected copolymer-1 with hydrobromic acid to form trifluoroacetyl copolymer-1, treating the trifluoroacetyl copolymer-1 with an aqueous piperidine solution to form copolymer-1, and purifying the copolymer-1 so as to result in copolymer-1 having the desired average molecular weight.

The present invention will further be described in the examples below. However, the present invention should not be construed as being limited thereby. Unless otherwise indicated, all parts, percentages, and the like, are by weight.

EXAMPLE 1

Antigens—Copolymer-1, which was prepared according to the method described in PCT/WO95/31990, was obtained from Teva Pharmaceutical Industries Ltd., Israel. GPBP was prepared from guinea pig spinal cord by acid extraction and ammonium sulfate precipitation as described in Hirshfeld H et al., *Febs Lett* (1970)

Animals—(PL/J×SJL/J) F1 female mice (8–10 weeks old) were obtained from Jackson Laboratories (Bar Harbor, Me.). Female Lewis rats (8–12 weeks old) were obtained from Harlan-Olac (Bicester, G. B.).

Induction and Assessment of EAE—Mice were injected with 200 µg GPBP emulsified in an equal volume of complete Freund's adjuvant (CFA) containing 4 mg/ml mycobacterium tuberculosis (H37Ra) (Difco Lab, Detroit, Mich.). The emulsion at a total volume of 0.1 ml was injected into all four footpads. Immediately after and 24 hours later, pertussitoxin (250 ng/mouse) (Sigma) was injected intravenously.

Rats were immunized with 25 µg of GPBP emulsified 1:1 in CFA containing 4 mg/ml H37Ra. The emulsion at a total volume of 0.1 ml. was injected into the two hindfoot pads.

Animals were examined daily from day 10 post induction for signs of disease. EAE was scored as follows: 0-no disease, 1-limp tail, 2-hind limb paralysis, 3-paralysis of all four limbs, 4-moribund condition, 5-death.

Induction of Oral Tolerance—Mice were fed with 250 µg GPBP or copolymer-1 dissolved in phosphate buffered saline (PBS) on days −7, −5, −3, 0, 2, 4 and 6 by gastric intubation with an 18gauge stainless steel feeding needle (Thomas). EAE was induced on day 0.

Rats were fed with 1 mg GPBP or copolymer-1 dissolved in PBS by gastric intubation using a sterile feeding tube (Uno Plast, Denmark). Rats were fed 5 times (total dose of 5 mg) before disease induction at intervals of 2–3 days. EAE was induced two days after the last feeding. Control mice and rats were mock fed with PBS.

Proliferation Assay—The proliferation response of spleen cells was tested 10–11 days after EAE induction as described above. Cells from 3 animals in each group were pooled and cultured in triplicate ($5 \times 10^5$ mouse cells and $2 \times 10^5$ rat cells) in microtiter plates with various antigen concentrations (GPBP) in a final volume of 0.2 ml. Microtiter plates contained RPMI 1640 (available from Sigma Biochemicals, St. Louis, Mo.) culture medium supplemented with 1% autologous serum. After 72 hr. of incubation, cells were pulsed with 1 µCi $\{^3H\}$-thymidine for 18 hr and then harvested onto filter papers and radioactivity was counted.

Cytokine Secretion Assay—Spleens were removed 10–11 days after EAE induction and cells of 3 mice from each group were pooled. Cells ($5 \times 10^6$/ml) were cultured in duplicates in 24 well plate in RPMI 1640 supplemented with 10% FCS (Fetal Calf Serum) in the presence or absence of antigen (GPBP 100 Fg/ml). Supernatants were harvested after 24–40 hr of culture. Quantitative ELISA for IL-2, IFN-γ, IL-4, IL-6 and IL-10 were performed using paired mAbs specific for the corresponding cytokines (Pharmingen, La Jolla, Calif.) according to the manufacturer's instructions.

Results

The efficacy of orally administered copolymer-1 in preventing the clinical manifestations of EAE in Lewis rats was compared to that of GPBP, when assayed under conditions previously reported to induce oral suppression by GPBP (P J Higgins & H L Weiner, *J Immunol* (1988) 140 440–445). The results summarized in Table 1 below demonstrate that copolymer-1 was more effective than GPBP and significantly decreased both the incidence (54% inhibition) and severity (57% inhibition) of EAE, as compared to PBS fed rats which served as control.

TABLE 1

Suppression of EAE in Rats by Oral Administration of Copolymer-1.

| Fed Antigen | Incidence | Mean Maximal Score ± SD | Mean Onset (days) |
|---|---|---|---|
| PBS (Control) | 27/28 (96%) | 1.8 ± 0.5 | 11.9 |
| GPBP | 10/17 (59%) (p = 0.0026) | 0.9 ± 0.5 | 11.4 |
| Copolymer-1 | 13/28 (46%) (p = 0.00005) | 0.78 ± 0.45 | 12.6 |

Each figure represents the cumulative results of 3–5 independent experiments. p values represent the statistical significance of difference from the control group (Fisher exact test). Mean maximal score was calculated for the entire group.

Figure 2:
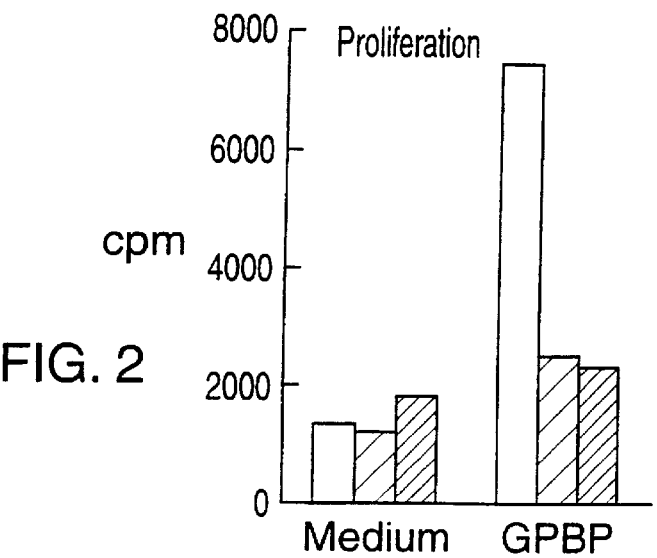

Effect of Antigen Feeding on the Immune Response to GPBP—The effect of oral administration of copolymer-1 and GPBP on the immune response to the disease inducing antigen-GPBP was tested in mice and rats. The results are summarized in FIG. 1 which shows the reduction in cell proliferation by each of the orally administered compounds (copolymer-1 or GPBP) in a rat spleen cell suspension stimulated with GPBP (FIG. 2 shows similar results from mice). As can be seen, oral administration of copolymer-1 resulted in almost complete inhibition of the proliferative responses to GPBP in these two species. In both species, copolymer-1 was more effective than GPBP in inhibiting the response to GPBP.

Figure 3:
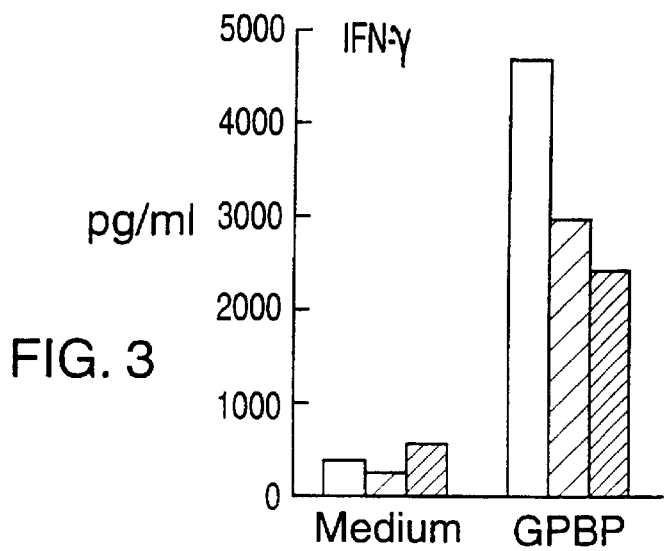
FIGS. 3 and 4 show the effect of copolymers on cytokine release.
Figure 4:
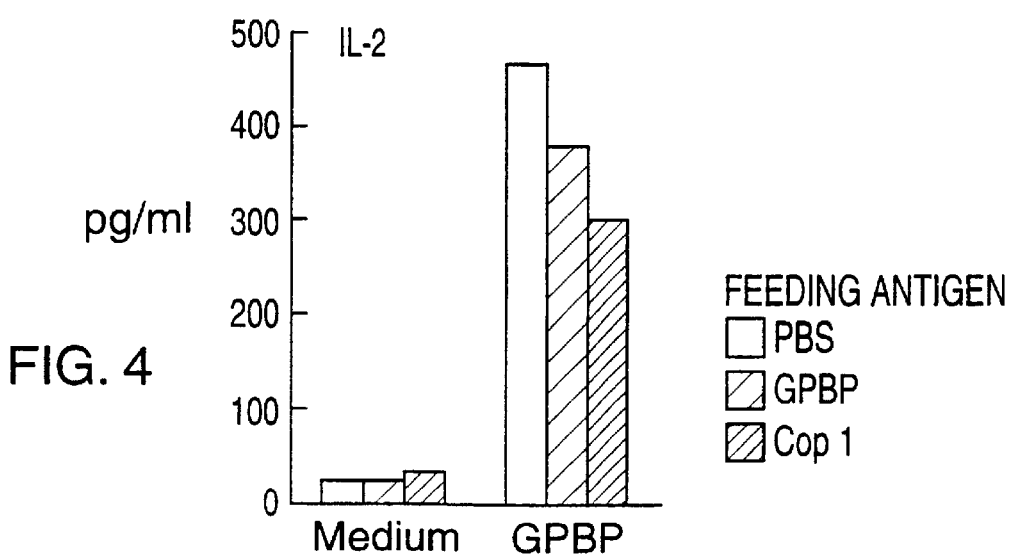

Cytokine levels were measured in the supernatants of spleen cell cultures derived from mice (FIGS. 3 and 4). Control mice fed with PBS secreted IL-2; IFN-γ and IL-6 (not shown) in response to GPBP. In mice fed with copolymer-1 or GPBP the amounts of the Th1 proinflammatory cytokines IL-2 and IFN-γ produced in response to GPBP stimulation were lower than in control groups, with copolymer-1 being a more effective suppressant. IL-4 and IL-10 were not detected with any group treatment.

The results demonstrate that copolymer-1 is effective in suppressing EAE when given orally. The clinically protective effect of orally administered copolymer-1 is associated with down regulation of T cell immune responses to GPBP such as proliferation and proinflammatory cytokines (IL-2 and IFN-γ) release.

EXAMPLE 2

Additional studies on the suppression of EAE by oral administration of copolymer-1 were performed in rats and mice. These studies established the optimal dose for treatment in each species. In order to understand the mechanism underlying oral suppression of EAE by copolymer-1, a copolymer-1 specific T-cell line was isolated from spleens of copolymer-1 fed animals. The in vitro reactivity of the lines and their in vivo effect on disease induction were studied.

Materials and Methods

Isolation of Copolymer-1 specific T cell lines—Lewis rats were fed 5 times with 1 mg copolymer-1 and (SJL/J×BALB/c)$F_1$ mice 7 times with 250 μg copolymer-1, at intervals of 2–3 days. Four to twelve days after the last feeding animals were sacrificed and their spleens removed.

Spleen cells of 3 animals were pooled and incubated (50×10$^6$/plate) with copolymer-1 (500 μg) in medium containing 1% autologous serum for 4 days. Every 14–21 days cells (4–6×10$^6$/plate) were restimulated by 3 days exposure to copolymer-1 (500 μg) presented on syngeneic irradiated (3000 rad) rat thymocytes (100×10$^6$/plate) or mouse splenocytes (50×10$^6$/plate). Stimulation was followed by propagation in 10% supernatant of Con A activated normal mouse spleen cells as T cell growth factor (TCGF).

Proliferation Assay—T cell lines (1×10$^4$ cells) were cultured with irradiated (3000R) thymocytes (rat-1×10$^6$) or splenocytes (mouse-5×10$^5$) and with the indicated antigens (10 μg copolymer-1; 1 μg Con A) in a final volume of 0.2 ml in microtiter plates. At the end of 48 hours incubation cultures were pulsed with $^3$H-thymidine and harvested 6–12 hours later.

Cytokine Assay—T cells of rat line (0.5×10$^6$/ml) were incubated with irradiated thymocytes (10×10$^6$) with or without the indicated antigen (50 μg copolymer-1, 5 μg Con A). Cells were cultured for 24 hours in RPMI 1640 supplemented with 10% FCS for IL-2, TNFα, IL-4 and IL-10-measurements and in serum free medium—DCCM-1 (Biological Industries, Kibbutz Beit Haemek, Israel) for 72 hours for TGFβ measurement.

Cytokine levels in supernatants were measured in a quantitative ELISA using pairs of monoclonal antibodies specific for the corresponding cytokines.

Induction of EAE—(SJL/×BALB/c)$F_1$ mice were injected in all four footpads with 2 mg mouse spinal cord homogenated (MSCH) emulsified in 1:1 ratio in CFA containing 1 mg/ml H37Ra (Difco Lab, Detroit, Mich). Pertussis toxin (250 ng/mouse, Sigma) was twice injected intravenously, once immediately after and again 48 hours later.

RESULTS

1. Dose response study in rats and mice

Rats were fed 5 times with 0.5, 1 or 2 mg copolymer-1 according to the established protocol (see Materials and Methods, above) and then challenged for EAE induction. The results are summarized in Table 2, and indicate that the most effective dose was 1 mg copolymer-1—0.5 mg or 2 mg copolymer-1 were less efficient in suppressing EAE.

Figure 5:
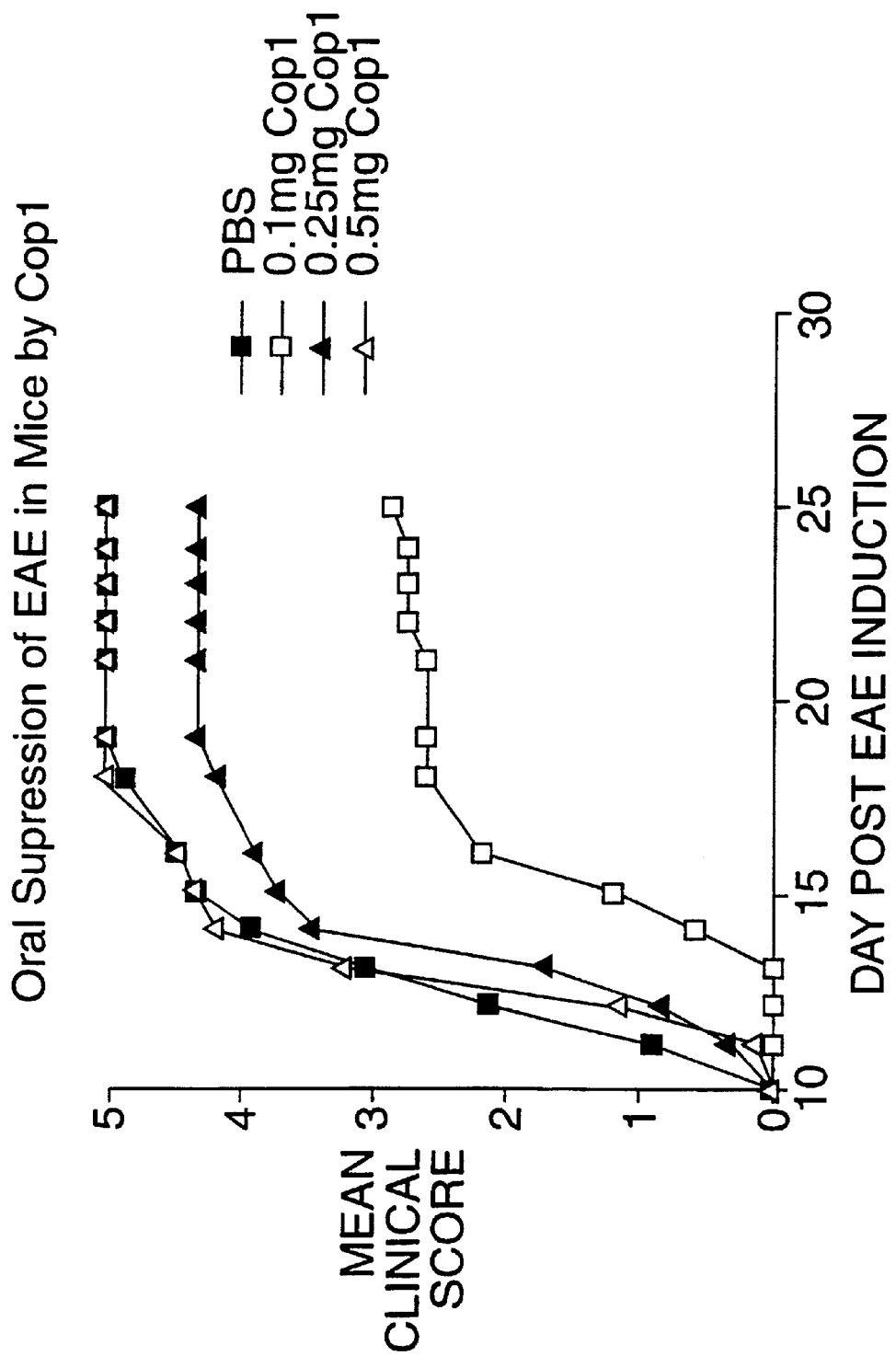
FIG. 5 shows the suppression of EAE in mice by orally-administered copolymer-1. (SJL/J×BALB/c)$F_1$ mice were fed with PBS (■), 0.1 mg copolymer-1 (□), 0.25 mg copolymer-1 (▲), or 0.5 mg copolymer-1 (△). Each dose was fed 7 times on days −7; −5; −3; 0; 2; 4 and 6. EAE was induced on day 0 by the injection of MSCH.

(SJL/J×BALB/c)$F_1$ mice were fed 7 times with 0.1, 0.25 or 0.5 mg copolymer-1 on days −7; −5; −3; 0; 2; 4 and 6 by gastric intubation. EAE was induced on day 0 by the injection of MSCH. The results summarized in FIG. 5 demonstrate that oral administration of copolymer-1 could suppress the disease in mice and the most effective dose was 0.1 mg copolymer-1. 0.25 mg of copolymer-1 was less effective and a dose of 0.5 mg was completely inactive. Thus, the results in both rats and mice demonstrate that oral copolymer-1 has an optimum dose response curve, and exceeding the effective oral dose resulted in inefficient suppression of EAE.

Figure 6:
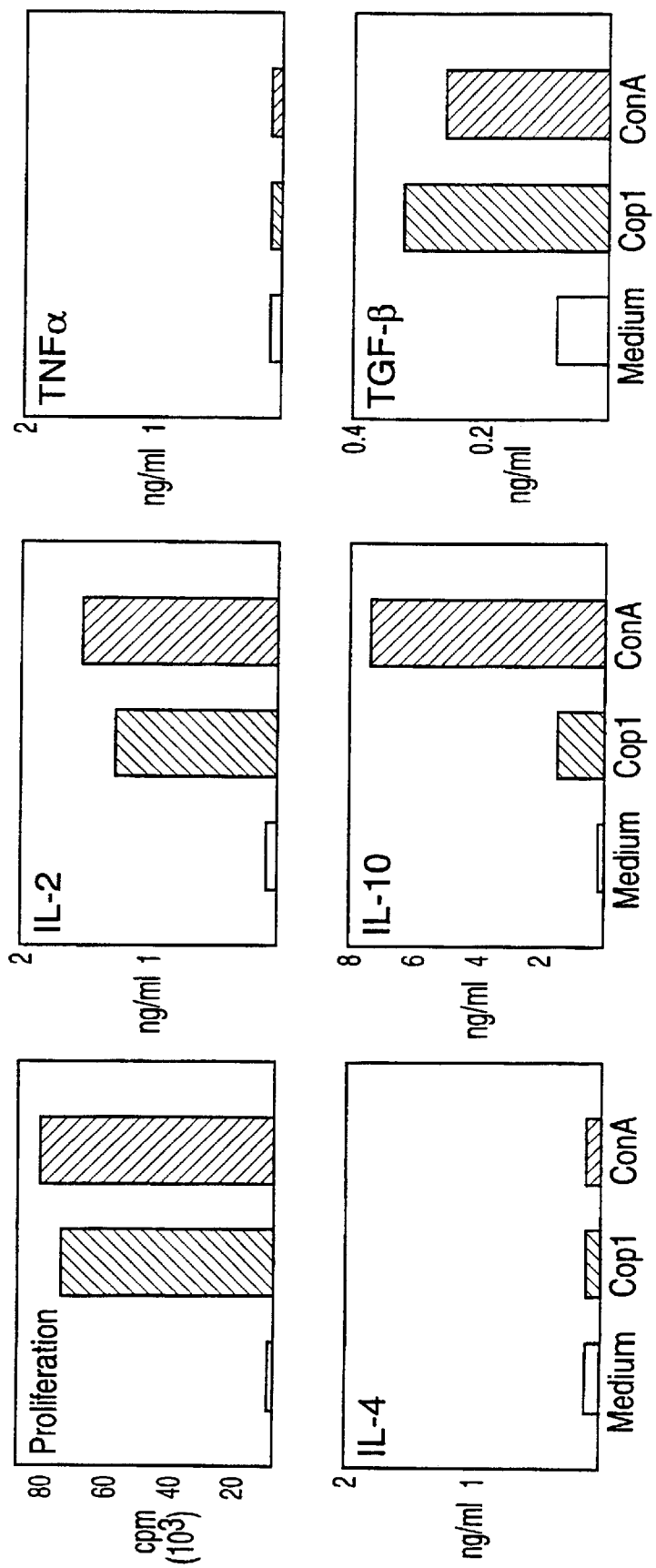
FIG. 6 shows the proliferation and cytokine secretion by T-cell line derived from spleens of copolymer-1 fed rats. Cells were cultured with medium copolymer-1 (50 μ/ml) or concavalin A (Con A) (5 μg/ml). The proliferation and cytokine secretion responses to these antigens were measured.

2. Studies with copolymer-1 specific Ts-lines established from copolymer-1 fed animals Copolymer-1 specific T suppressor cell lines were isolated from spleens of rats and mice rendered unresponsive to EAE by feeding with copolymer-1. The proliferation and cytokine secretion response of such line isolated from rats is demonstrated in FIG. 6. This line proliferated in response to copolymer-1 and secreted IL-2, some IL-10 and TGFβ but not TNFα or IL-4. This cytokine profile is compatible with Th3 type cells which were shown to be induced by oral MBP (Chen et al. Science 265, 1237, 1994).

Figure 7:
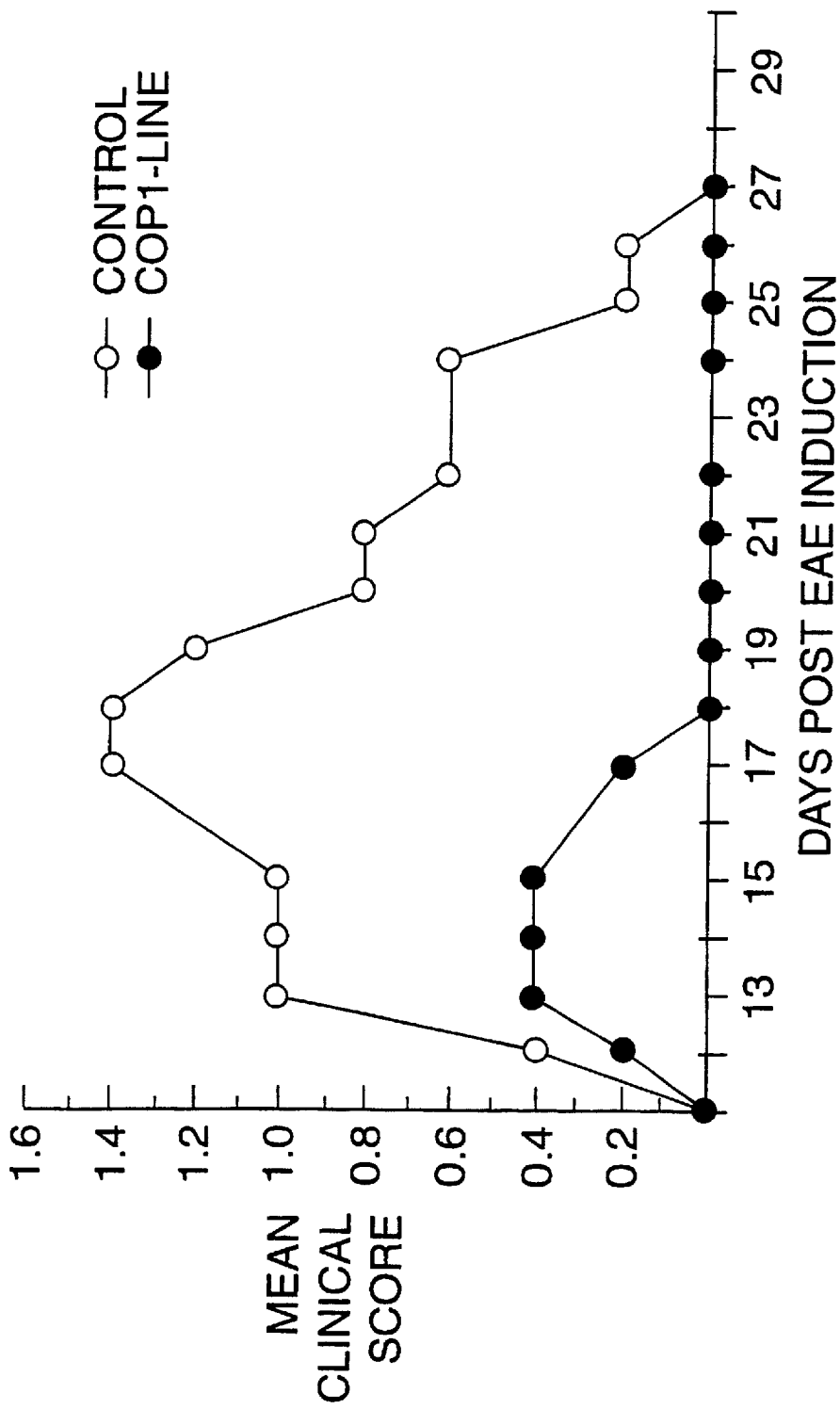
FIG. 7 shows the inhibition of EAE by T-cell line derived from spleens of copolymer-1 fed rats. Cells (20×10$^6$/rat) were injected intraperitoneally 3 days after stimulation with copolymer-1, followed by EAE induction.
Figure 8:
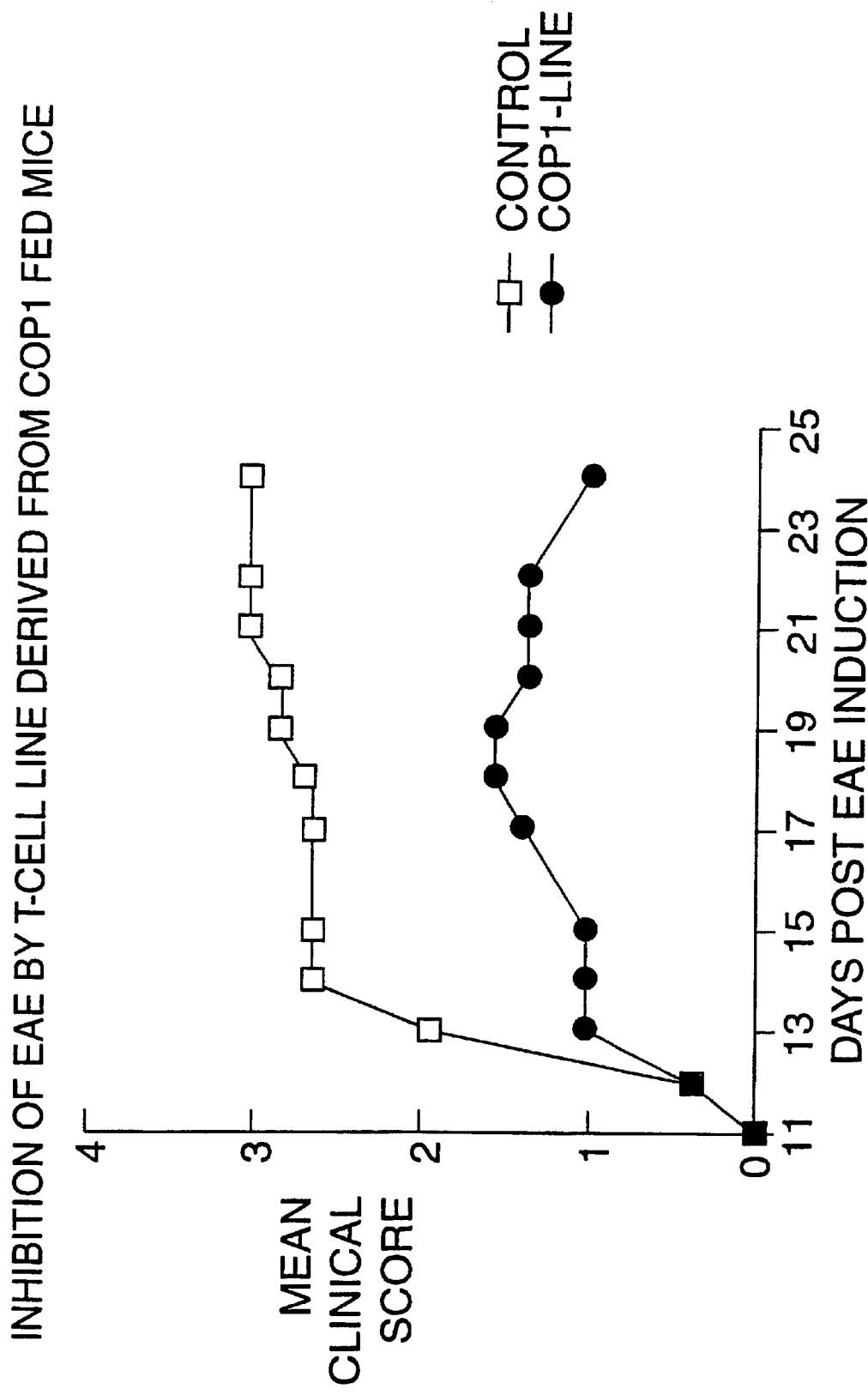
FIG. 8 shows the inhibition of EAE by T-cell line derived from spleens of copolymer-1 fed mice. Cells (15×10$^6$/mouse) were injected intravenously 3 days after stimulation with copolymer-1, followed by EAE induction.

The ability of the copolymer-1 specific lines to prevent EAE in vivo was studied. Cell lines were injected 3 days after in vivo stimulation with copolymer-1 ($20\times10^6$ cells/rats injected i.p. and $15\times10^6$ cells/mouse injected i.v.). The animals were challenged for EAE induction immediately following cell transfer. The results illustrated in FIGS. 7 and 8 demonstrate that the disease was considerably inhibited in the recipient animals. Thus, both the rat and murine copolymer-1 T-cell lines adoptively transferred the unresponsiveness to EAE induced by oral administration of copolymer-1. These cells actively down regulate the pathological immune response in vivo.

TABLE 2

Dose Response Study of Oral Copolymer-1 in Rats

| Fed Antigen | Incidence | Mean Score ± SD | Mean Onset | Suppression* (%) |
|---|---|---|---|---|
| PBS (control) | 10/11 | 1.32 ± 0.64 | 13.1 | |
| Copolymer-1 (0.5 mg) | 9/11 | 0.95 ± 0.57 | 13.5 | 28 |
| Copolymer-1 (1 mg) | 7/11 | 0.64 ± 0.50 | 15.1 | 51 |
| Copolymer-1 (2 mg) | 8/11 | 0.91 ± 0.70 | 13.1 | 31 |

*calculated by mean score.

Each incidence figure represents the cumulative results of 2 individual experiments. Mean maximum clinical score was calculated for the whole group.

EXAMPLE 3

The effect of the oral administration of copolymer-1 on the induction of EAE in Rhesus monkeys was studied.
Materials Copolymer-1 was provided by Teva Pharmaceutical Industries Ltd. in an enteric-coated hard gelatin capsule comprising two dosage levels: 1 mg of copolymer-1 and 20 mg of copolymer-1. Each dosage level was formulated using mannitol, and coated with Eudragit L30D55. Placebo or control capsules comprised capsules containing 5 mg of sugar.

Bovine MBP was purchased from Life Technologies, Grand Island, N.Y. This material represents a highly purified preparation that gives a single band at 18.5 Kd following SDS-PAGE and Silver staining.
Feeding Protocol 3 Rhesus monkeys were treated as follows: One monkey served as control and was fed with placebo capsules (containing 5 mg glucose only). The second and third monkeys were fed with copolymer-1-containing capsules at a dose of 1 mg/feeding and 20 mg/feeding, respectively. Animals were fed every other day for a total of 10 feedings: 5 times prior to disease induction (immunization on day 0) and then 5 times after immunization.
Disease Induction Disease was induced on day 0 by an intradermal injection of 8 mg bovine—MBP and 3 mg H37Ra *M. tuberculosis* in FCA into the hind footpads, total injected volume between 0.1 and 0.15 ml per footpad. The animals were followed for clinical manifestations of EAE, a variety of serum and CSF immunological markers and spinal cord and cranial MRI's.

Clinical Scoring

Symptom scores were given as follows: 0, normal neurological exam; 1, weight loss, anorexia, yawning, slow responses to stimuli, irritability or lethargy; 2, mild neurological signs, indifference, drooling, clumsiness using limbs, tremors, altered cry and disordered gaze; 3, moderate neurological signs, blindness (pupils do not react to light), akinesia, leg weakness, or paralysis; 4, severe neurological signs, semicoma, coma, quadriplegia; 5, death.
Antigen-induced Lymphocytes Proliferation Heparinized blood samples were diluted 1:1 with Hanks balanced salt solution (BSS) containing 5% heat inactivated fetal calf serum (FCS), and layered in a hypaque-ficol gradient. Centrifugation (2000 rpm for 20 minutes at room temperature) allowed recovery of diluted plasma and the separation of lymphocytes at the interface. The recovered lymphocytes were washed three times in Hanks BSS-5% FCS and resuspended in RPMI 1640 complete medium containing RPMI 1640 medium, 10% FCS, and 1% of the following reagents: non-essential amino acids, sodium pyruvate, L-glutamine, 2-mercaptoethanol, and penicillin/streptomycin. The recovered lymphocytes were counted and resuspended at a final concentration of $2\times10^6$/ml. Cultures containing 100 microliters of the cell suspension and 100 microliters of MBP (20 micrograms/well), 100 microliters of copolymer-1 (10 micrograms/well) or 100 microliters of Con A (1 microgram/well) were set up in round bottom 96 well microtiter plates. The cultures were maintained at 37° C. in 5% $CO_2$ for 6 days. On day 5 of culture, each well was pulsed with 1 μCi of $^3$H-thymidine for 16 to 18 hours. On day 6, the cultures were harvested by an automatic cell harvester, and counted by liquid scintillation methods. Stimulation indices were determined as follows:

$$\text{Stimulation index} = \frac{\text{Experimental cpm} - \text{background cmp}}{\text{background cmp}}$$

Clinical Results

Figure 9:
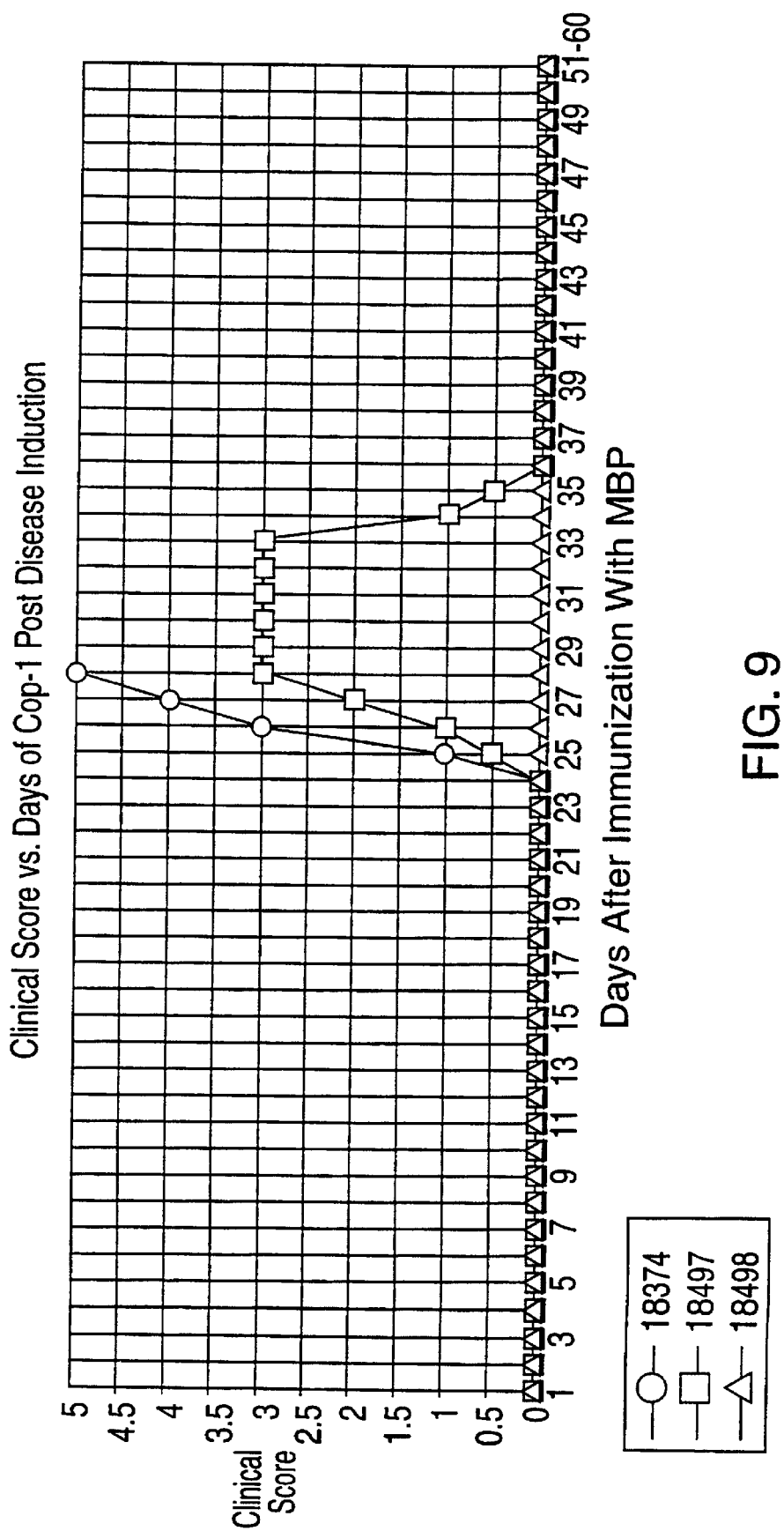
FIG. 9 shows the Clinical Scores vs. Days of Copolymer-1 Post EAE Disease Induction in three Rhesus Monkeys.

No animal exhibited clinical symptoms for 24 days. The placebo-treated animal 18374 developed disease on day 25, and due to severe manifestations of EAE (score=$4^+$ on a scale of 5) had to be sacrificed on day 28. The high-dose copolymer-1 treated animal 18498 treated with 20 mg of copolymer-1 did not show any significant clinical symptoms over the 60 day observation period. The low-dose copolymer-1 treated animal 18497 began to show minimal symptoms on day 25, however, in contrast with the placebo-treated animal 18374, '497 showed a much slower increase in clinical symptoms and leveled off at 2 to 3+ from day 28 to day 33. At this time-point animal '497 was fed with 20 mg capsules 5 times on alternate days for a total of 10 days. As can be seen in FIG. 9, within 3 days the animal's clinical signs dropped to zero and remained there until the two copolymer-1 fed animals '497 and '498 were sacrificed on day 60 for histology.
Flow Cytometry The Epics C flow cytometer was used to analyze both peripheral blood lymphocytes (PBL) and cerebral spinal fluid (CSF) collected from each monkey. The red blood cells were lysed and the remaining white blood cells (WBCs) were washed and stained using standard methods with appropriate reagents. Tables 3 and 4 below show the data from staining PBL and CSF WBCs from the three animals in this Example.

The number of cells staining CD4+ was slightly greater in copolymer-1 fed animals 18497 and 18498 than in the control animal 18374. The number of CD4+ cells that are also CD45RA− appears to increase in both control animal 18374 and low-dose copolymer-1 fed animal 18497 about the time both animals exhibited clinical symptoms (days +27 to +34), but remained fairly constant in the high-dose copolymer-1 fed animal 18498. The number of CD8+ CD45RA+ staining cells decreased steadily in control animal 18374 and low-dose copolymer-1 fed animal 18497, but increased slightly in high-dose copolymer-1 fed animal 18498 (indicating the production of new CD4+ cells).

The number of cells found in the CSF of the control animal 18374 increased steadily from day 20+ until day 28+ when the animal died. Analysis showed that most of the CD4+ cells were CD45RA−. The number of cells collected from the CSF of animal 18497 were too few to count or stain. The number of cells collected from animal 18498 were too few to count or stain except on day +27. The CD4+ cells collected then were predominantly CD45RA−.

TABLE 3

Analysis of PBL obtained from Rhesus Monkeys immunized with MBP.

| Monkey | (Day of study) | CD4+ | CD8+ | Ratio | CD4+ CD45RA+ | CD8+ CD45RA+ |
|---|---|---|---|---|---|---|
| 18374 (control) | (−1) | 24 | 47 | 0.51 | 15 | 45 |
| | (+6) | 24 | 42 | 0.57 | 15 | 40 |
| | (+13) | 23 | 40 | 0.58 | 12 | 38 |
| | +20 | 22 | 45 | 0.49 | 10 | 45 |
| | +27 | 24 | 27 | 0.89 | 10 | 23 |
| | +28 | 24 | 24 | 1.0 | 10 | 21 |
| 18497 (1 mg Copolymer-1/dose) | −1 | 35 | 36 | 0.97 | 21 | 33 |
| | +6 | 39 | 31 | 1.26 | 24 | 29 |
| | +13 | 37 | 34 | 1.09 | 16 | 29 |
| | +20 | 41 | 32 | 1.28 | 18 | 25 |
| | +27 | 35 | 27 | 1.3 | 12 | 18 |
| | +34 | ND | ND | ND | ND | ND |
| 18498 (20 mg Copolymer-1/dose) | −1 | 37 | 40 | 0.93 | 23 | 32 |
| | +6 | 37 | 42 | 0.88 | 23 | 32 |
| | +13 | 41 | 46 | 0.89 | 24 | 37 |
| | +20 | 27 | 57 | 0.47 | 12 | 41 |
| | +27 | 37 | 52 | 0.71 | 22 | 41 |
| | +34 | ND | ND | ND | ND | ND |

ND = not determined

TABLE 4

Analysis of CSF obtained from Rhesus Monkeys immunized with MBP.

| Animal | (Day of study) | Cells μl | CD4+ | CD8+ | CD4+:CD8+ Ratio | CD4+ CD45RA+ | CD8+ CD45RA+ |
|---|---|---|---|---|---|---|---|
| 18374 | 0 | ND | too few cells | | | | |
| | +14 | 28 | too few | | | | |
| | +20 | 100 | 61 | 18 | 2.18 | 2 | 4 |
| | +28 | 294 | 35 | 35 | 0.94 | 4 | 8 |
| 18497 | 0 | too few cells | | | | | |
| | +14 | too few cells | | | | | |
| | +20 | too few cells | | | | | |
| | +27 | too few cells | | | | | |
| | +34 | too few cells | | | | | |
| 18498 | 0 | too few cells | | | | | |
| | +14 | too few cells | | | | | |
| | +20 | too few cells | | | | | |
| | +27 | 29.7 | 47 | ND | 8 | ND | |
| | +34 | too few cells | | | | | |
| | +41 | too few cells | | | | | |

ND = not determined

Analysis For Antigen-specific T cell suppressor factor inducer (Tcsfi)

The analysis for MBP-specific Tsfi in the plasma of the three monkeys in this Example are seen in Tables 5 and 6 below. None of the animals produced MBP-specific Tsfi until day +13 following EAE induction with MBP. Control animal 18374 did not produce any Tsfi until day +20, and the level produced thereafter was just above background. Copolymer-1 fed animals 18497 and 18498 consistently produced significant levels of Tsfi from day +13 until day +41 shortly before termination.

Table 6 shows that plasma samples which did not contain Tsfi did not react with anti-TGF-beta antibody. Plasma which exhibited MBP-binding with 3C9 antibody (anti-Tsfi) also reacted with the anti-TGF-beta antibody. Recombinant human TGF-beta reacted with the anti-TGF-beta, but not 3C9 antibody.

TABLE 5

Assay for MBP-specific T suppressor Inducer factor[a]

| Animal # | −13 | −1 | +6 | +13 | +20 | +27 | +34 | +41 |
|---|---|---|---|---|---|---|---|---|
| 18374 | none | none | ND | ND | .17 | .21 | died | |
| 18497 | none | none | none | .60 | .61 | .56 | .66 | .76 |
| 18498 | none | none | none | .32 | .32 | .42 | .40 | .40 |

[a]Data represents OD at 405 nm, of plasma samples at a 1:20 dilution
ND = Not Determined

TABLE 6

The association between MBP-specific Tsfi and TGF-beta in plasma of Rhesus Monkeys treated with copolymer-1.

| Animal # | Day of study | anti-Tsfi (3C9 Ab)[a] | anti-TGF-beta[b] |
|---|---|---|---|
| 18374 | −1 | none | none |
| | +27 | 0.21 | none |
| 18497 | +6 | none | none |
| | +13 | 0.60 | 0.71 |
| | +27 | 0.56 | 0.65 |
| | +41 | 0.76 | 0.85 |
| 18498 | +6 | none | none |
| | +13 | 0.32 | 0.35 |
| | +27 | 0.42 | 0.47 |
| | +41 | 0.40 | 0.45 |
| | r human TGF-beta[c] | — | 0.72 |

[a]Represents OD405 nm of material bound for MBP (2.5 μg of protein) and reacts with the anti-human Tsfi (3C9) antibody.
[b]Represents OD405 nm of material bound to MBP and reacts with anti-human TGF-beta antibody.
[c]Represents well coated with 100 ng of recombinant human TGF-beta.

EXAMPLE 4

Six monkeys were treated and subsequent analyses performed substantially according to the protocol described for Example 3 hereinabove.

Control placebo-fed animal 18746 was fed with capsules containing glucose. Animal 18586 was fed with 1 mg copolymer-1 in capsules with cracked enteric coating. Animal 18639 was fed with 20 mg copolymer-1 in capsules with cracked enteric coating. Animal 18724 was fed with 1 mg copolymer-1 in intact enteric coated capsules. Animal 18810 was fed with 10 mg copolymer-1 in intact enteric coated capsules. Animal 18962 was fed with 20 mg copolymer-1 in intact enteric coated capsules.

The schedule of feeding, disease induction and follow-up were substantially the same as those of Example 3 described hereinabove.

Results

As can be seen with reference to FIG. 10, control monkey 18746 developed acute disease beginning on day +21 and died on day +23 of disease manifestations. Animals 18586 and 18639 treated with the "cracked" enteric coating, which opened in the stomach (at both doses), were not protected from the disease and died within 2–3 days of disease manifestations. All the monkeys fed with copolymer-1 in enteric coated capsule were fully protected from the disease, and developed no signs of EAE until day 60, when they were sacrificed for histology.

What is claimed is:

1. A method of treating multiple sclerosis comprising ingestion or inhalation of a therapeutically effective amount of copolymer-1 (glatiramer acetate).

2. A method according to claim 1, wherein the therapeutically effective amount of copolymer-1 (glatiramer acetate) is from 0.1 to 1000 mg/day.

3. A method in accordance with claim 1, wherein said copolymer-1 (glatiramer acetate) is administered orally.

4. A method in accordance with claim 1, wherein said copolymer-1 (glatiramer acetate) is administered nasally.

5. A method in accordance with claims 3 or 4, wherein said copolymer-1 (glatiramer acetate) is inhaled.

6. A method in accordance with claim 3, wherein said copolymer-1 (glatiramer acetate) is orally administered in an enterically-coated form.

7. The use of copolymer-1 (glatiramer acetate) for the manufacture of a medicament for the treatment of multiple sclerosis, wherein said medicament is administered through ingestion or inhalation.

8. The use as claimed in claim 7, wherein the medicament comprises from 0.1 to 1000 mg/day of copolymer-1 (glatiramer acetate).

9. The use according to claims 7 or 8, wherein the medicament is formulated for oral or nasal administration.

10. The use according to claim 9, wherein said administration is by inhalation.

11. The use according to claim 9, wherein the medicament is enterically-coated.

12. A pharmaceutical composition for the treatment of multiple sclerosis comprising a therapeutically effective amount of copolymer-1 (glatiramer acetate) and a pharmaceutically acceptable carrier, wherein said pharmaceutical composition is formulated for administration by either ingestion or inhalation.

13. The pharmaceutical composition of claim 12, wherein said pharmaceutical composition is in solid form, liquid form, aerosol or inhalable powder.

14. The pharmaceutical composition of claim 13, wherein said solid form is enterically-coated.

15. A method of treating multiple sclerosis in a subject comprising the administration of a therapeutically effective amount to the subject of the pharmaceutical composition claimed in any one of claims 12 to 14.

* * * * *